(12) United States Patent
Herrmann et al.

(10) Patent No.: US 8,153,810 B2
(45) Date of Patent: *Apr. 10, 2012

(54) ALKYLIDENE COMPLEXES OF RUTHENIUM CONTAINING N-HETEROCYCLIC CARBENE LIGANDS; USE AS HIGHLY ACTIVE, SELECTIVE CATALYSTS FOR OLEFIN METATHESIS

(75) Inventors: Wolfgang Anton Herrmann, Freising (DE); Wolfgang Schattenmann, Burghausen (DE); Thomas Weskamp, Sta. Clara, CA (US)

(73) Assignee: Evonik Degussa GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/090,688

(22) Filed: Apr. 20, 2011

(65) Prior Publication Data
US 2011/0282068 A1 Nov. 17, 2011

Related U.S. Application Data

(60) Continuation of application No. 12/875,659, filed on Sep. 3, 2010, now abandoned, which is a continuation of application No. 12/692,229, filed on Jan. 22, 2010, now abandoned, which is a continuation of application No. 11/021,967, filed on Dec. 23, 2004, now Pat. No. 7,652,145, which is a division of application No. 10/630,552, filed on Jul. 29, 2003, now Pat. No. 7,294,717, which is a division of application No. 09/647,742, filed as application No. PCT/EP99/01785 on Mar. 18, 1999, now Pat. No. 6,635,768.

(51) Int. Cl.
C07F 15/00 (2006.01)
C07C 2/02 (2006.01)
C07C 6/00 (2006.01)

(52) U.S. Cl. ......... 548/103; 556/136; 585/375; 585/643

(58) Field of Classification Search .................. 548/103; 556/136; 585/375, 643
See application file for complete search history.

(56) References Cited

U.S. PATENT DOCUMENTS

| | | | |
|---|---|---|---|
| 5,312,940 A | 5/1994 | Grubbs et al. |
| 5,342,909 A | 8/1994 | Grubbs et al. |
| 5,728,839 A | 3/1998 | Herrmann et al. |
| 5,728,917 A | 3/1998 | Grubbs et al. |
| 6,025,496 A | 2/2000 | Herrmann et al. |
| 6,426,419 B1 | 7/2002 | Grubbs et al. |
| 6,552,139 B1 | 4/2003 | Herrmann et al. |
| 6,635,768 B1 | 10/2003 | Herrmann et al. |
| 6,787,620 B2 | 9/2004 | Herrmann et al. |
| 7,294,717 B2 | 11/2007 | Herrmann et al. |
| 7,329,758 B1 | 2/2008 | Grubbs et al. |
| 7,378,528 B2 | 5/2008 | Herrmann et al. |
| 7,652,145 B2 | 1/2010 | Herrmann et al. |
| 2005/0049417 A1 | 3/2005 | Arlt |
| 2005/0261451 A1 | 11/2005 | Ung et al. |
| 2006/0128912 A1 | 6/2006 | Piers et al. |
| 2006/0287450 A1 | 12/2006 | Kohler et al. |
| 2006/0293526 A1 | 12/2006 | Koehler et al. |

FOREIGN PATENT DOCUMENTS

| | | |
|---|---|---|
| DE | 4447066 A1 | 7/1996 |
| EP | 0721953 A1 | 7/1996 |
| WO | WO-96/04289 A1 | 2/1996 |
| WO | WO-97/06185 A1 | 2/1997 |
| WO | WO-97/34875 A1 | 9/1997 |

OTHER PUBLICATIONS

Evonik original complaint against Materia Aug. 26, 2009.
Materia's Answer with Counterclaims, Oct. 29, 2009.
Evonik's Response to the Counterclaims, Nov. 18, 2009.
Evonik's Complaint Against Materia and Elevance, Mar. 11, 2010.
Materia's Answers to Evonik's New Complaint and Counterclaims with UNO for Infringement, Jun. 3, 2010.
Evonik's Answers to UNO's Infringement Allegations, Sep. 23, 2010.
Materia's Amends Its Complaint to Allege Inequitable Conduct, Feb. 2, 2011.
Evonik's Answers to the Inequitable Conduct Allegations, Feb. 15, 2011. Van Der Eide, et al., Mechanistic insights into the ruthenium-catalysed diene ring-closing metathesis reaction, Nature Chemistry (May 9, 2010), Advance Online Publication, pp. 1-6.
Alder, et al., "Bis(diisopropylamino)carbene," *Angew. Chem. Int. Ed. Eng.* ((1996), vol. 35, No. 10, pp. 1121-1123.
Arduengo, et al., "Auf der Suche nach stabilen Carbenen," *Chemie in unserer Zeit* (1998), vol. 32, pp. 6-14.

(Continued)

*Primary Examiner* — Porfirio Nazario Gonzalez
(74) *Attorney, Agent, or Firm* — Connolly Bove Lodge & Hutz LLP

(57) ABSTRACT

The invention relates to a complex of ruthenium of the structural formula I,

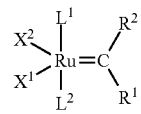

where $X^1$ and $X^2$ are identical or different and are each an anionic ligand,
$R^1$ and $R^2$ are identical or different and can also contain a ring, and $R^1$ and $R^2$ are each hydrogen or/and a hydrocarbon group,
the ligand $L^1$ is an N-heterocyclic carbene and the ligand $L^2$ is an uncharged electron donor, in particular an N-heterocyclic carbene or an amine, imine, phosphine, phosphate, stibine, arsine, carbonyl compound, carboxyl compound, nitrile, alcohol, ether, thiol or thioether,
where $R^1$, $R^2$, $R^3$ and $R^4$ are hydrogen or/and hydrocarbon groups.
The invention further relates to a process for preparing acyclic olefins having two or more carbon atoms or/and cyclic olefins having four or more carbon atoms from acyclic olefins having two or more carbon atoms or/and from cyclic olefins having four or more carbon atoms by an olefin metathesis reaction in the presence of at least one catalyst, wherein a complex is used as catalyst and $R'^1$, $R'^2$, $R'^3$ and $R'^4$ are hydrogen or/and hydrocarbon groups.

35 Claims, 2 Drawing Sheets

OTHER PUBLICATIONS

Arduengo, et al., "A Stable Crystalline Carbene," *J. Am. Chem. Soc.* (1991), vol. 113, pp. 361-363.

Cardin, et al., "An Electron-rich Olefin as a Source of Co-ordinated Carbene; Synthesis of *trans*-PtCl$_2$[C(NPhCH$_2$)$_2$]PEt$_3$," *J. Chem. Soc*, Section D (1971), pp. 400-401.

Cardin, et al., "Carbene Complexes. Part I. Electron-rich Olefins as a Source of Carbene Complexes of Platinum(II) and Palladium(II); and Some Experiments with (CF$_3$)$_2$CN$_2$," *J. Chem. Soc., Dalton Trans.* (1973), pp. 514-522.

Fröhlich, et al., "Carbenes as Pure Donor Ligands: Theoretical Study of Beryllium-Carbene Complexes," *Organometallics* (1997), vol. 16, pp. 442-448.

Herrmann, et al., "Einfache Synthese eines präparativ nützlichen Alkoxy(carbonyl)metallats," *Chem. Ber.* (1991), vol. 125, pp. 1795-1799.

Kreiter, et al., "Chrom-, Molybdän- and Wolframkomplexe mit 1,3-Dimethyl-4-imidazolin-2-yliden-Liganden," *Chem. Ber.* (1976), vol. 109, pp. 1749-1758.

Öfele, et al., "Tetracarbonyl-bis(1,3-dimethyl-4-imidazolin-2-yliden)-chrom(0)," *Angew. Chem.* (1970), vol. 82, pp. 775-776.

Öfele, et al., "(1.4-Dimethyl-tetrazolin)-carbonylferrate, Ausgangsprodukte für (11.4-Dimethyl-tetrazolinyliden)- und Bis(methylamino)carben—Komplexe," *Chem. Ber.* (1972), vol. 105, pp. 529-540.

Öfele, et al., "Photo-induced Substitution and Isomerisation in Octahedral *cis*-Dicarbene Complexes," *Z Naturforsch* (1976), vol. 28B, pp. 306-309.

Öfele, et al., "Isomerisation of cis- and trans-Dicarbene Comoplexes of the Type M(CO)$^4$L$_2$ (M = Cr, Mo, W)," *Z Naturforsch* (1976), vol. 31B, pp. 1071-1077.

Öfele, "1,3-Dimethyl-4-Imidazolinyliden-(2)-Pentacarbonylchrom Ein Neuer Übergangsmetall-Carben-Komplex," *J. Organometal. Chem.* (1968), vol. 12, pp. 42-43.

Dutt, "2 : 5-Iminodihydro-1 : 2 : 3-triazole. Part I. Constitution of Dimroth's 5-Anilinotriazole," *J. Chem. Soc. Transactions* 1923, pp. 265-274.

Scarpati, et al., "Reazione fra fenilazide e chetenacetali bisostituiti: sintesi degli acetali dei triazoloni-4," *Gazz. Chim. Ital.* (1963), vol. 93, pp. 942-948.

Busch, et al., "Mitteilungen aus dem chemischen Laboratorium der Universität Erlangen," J. Practical Chem. (1911), pp. 425-453.

Page 28 from Patent Interference No. 105,372.
Paper 29 from Patent Interference No. 105,372.
Paper 56 from Patent Interference No. 105,373.

Kocher, "Neue Wege zu N-heterocylischen Carbenen und deren Metalkomplexen; Anwendungen in der Homogenkatalyse", Dissertation, Technische Universitat Munchen, 1997, Seiten 31-59; 124-147; 158-173.

Preliminary Assessment—Annex to summons for oral proceeding.
Materia Inc.'s submission in EP 1,087,838 dated Nov. 21, 2007.
Materia Inc.'s submission in EP 1,087,838 dated Dec. 14, 2007.
Materia Inc.'s submission in EP 1,087,838 dated Jul. 9, 2008.

Schattenmann, "Neue Katalysatoren fur die Olefin-Metathese", Dissertation an der Fakultat fur Chemie, Biologie und Geowissenschaft der TU Muchen, 1998, Seiten 157-240, & TU Jahrbuch 1997, Seite 580.

Weskamp, T. et al., Angew. Chem. Int. Ed, 37:2490-2493, "A Novel Class of Ruthenium Catalysts for Olefin Metathesis", 1998.

Kocher: "Neue Wege zu N-Heterocylischen Carbenen und deren Metalkomplexen; Anwendungen in der Homogenkatalyse", Dissertation, Technische Universitat Munchen, 1997; complete Dissertation.

Schattenmann: "Neue Katalysatoren fur die Olefin-Metalhese", Dissertation, Technische Universitat Munchen, 1997; complete Dissertation.

Schwab et al., "A Series of Well-Defined Metathesis Catalysts Synthesis of [RhCl2(=CHR)(PR2)2] and Its Reactions, "Angew. Chem. Int. Ed. Engl., 1995, 34(18), 2039-2041.

Schwab et al., "Synthesis and Applications of RuCl2(=CHR)(PR3)2: The Influence of the Alkylidene Moiety on Metathesis Activity," *J. Am. Chem. Soc.*, 1996, 118(1), 100-110.

Arduengo et al., "Electronic Stabilization of Nucleophilic Carbenes," J. Am. Chem. Soc., 1992, 114(14), 5530-5534.

Enders et al., "Preparation, Structure, and Reactivity of 1,2,4-Triphenyl-4, 5-dihydro- 1H-1,2,4-triazol-5-ylidene, a New Stable Carbene," Angew, Chem. int. Ed. Engl., 1995, 39(9), 1021-1023.

Herrmann et al., "Oxy Funtionalization of Metal-Coordinated Heterocyclic Carbenes, " Organometallics, 1995, 14(3), 1085-1086.

Herrmann et al., Functionalized imidazoline-2-ylidene complexes of rhodium and palladium, J. Organomet. Chem., 1997, 547, 357-366.

Dias et al., "Well-Defined Ruthenium Olefin Matathesis Catalysts: Mechanism and Activity," J. Am. Chem. Soc., 1997, 119(17), 3887-3897.

Jinkun Huang et al.: "Olefin Metathesis—Active Ruthenium Complexes Bearing a Nucleophilic Ligand", J. Am. Chem. Soc., 1999, 121(12), 2674-2678; XP002928348; vorausveroffenlicht im Internet am 11. Marz 1999.

Herrmann et al.: "N-Heterocyclic Carbenes", Agnew. Chem. Int. Ed. Engl., 1997, 36(20), 2162-2187; XP2178612.

Herrmann: "N-Heterocyclic Carbenes: A New Concept in Organometallic Catalysis", Agnew. Chem. Int. Ed., 2002, 41(8), 1290-1309; XP1111697.

Weskamp: "N-heterocylische Carbene: Eine neue Generation von Rutheniumkatalysatoren fur de Olefin-Metathesis", Dissertation, Technische Universitat Munchen, Nov. 5, 1999 (Datum der Annahme durch Fakultat).

Enders et al.: "Immobilized Triazolium Salts as Precursors to Chiral Carbenes-Rhodium-Catalyzed Asymmetric Hydrosilylation as a First Test Reaction", Molecules Online, 1998, 2, 105-108; Jul. 9, 1998 (http://www.springer/link.com/content/nnn9j6d7q2d1p04c/fulltext.pdf,heruntergeladen am Dec. 9, 2007).

Bergbreiter et al: "Self-Serparating Homogeneous Copper (I) Catalysts", J. Chem. Soc., 2007, 129(35), 10666-10667; Aug. 4, 2007.

Rostovtsev et al: "A Stepwise Huisgen Cycloaddition Process: Copper (I)-Catalyzed Regioselective "Ligation" of Azides and Terminal Alkyes", Agnew. Chem. Int. Ed. 2002, 41(14), 2596-2599; XP002331267; Jul. 15, 2002.

Chan et al.: "Polytriazoles as Copper(I)-Stabilizing Ligand in Catalysis", Org. Lett., 2004, 6(17), 2853-2855; Jul. 30, 2004.

Dai et al: "Triazole-Based Monophosphine Ligands for Palladium-Catalyzed Cross-Coupling Reactions of Aryl Chlorides", J. Org. Chem., 2006, 71(10), 3928-3934; Apr. 13, 2006.

Detz et al: "Clickphine: A Novel and Highly Versatile P,N Ligand Class via Click Chemistry", Org. Lett., 2006, 8(15), 3227-3230; Jun. 27, 2006.

Mindt et al: "Click to Chelate: Synthesis and Installation of Metal Chelates into Biomolecules in a Single Step", J. Am. Chem. Soc., 2006, 128(47), 15096-15097:Nov. 3, 2006.

Crudden et al: "Stability and reactivity of N-heterocyclic carbene complexes", Coordination Chemistry Reviews 2004, 248(21-24), 2247-2273; XP004917429; Aug. 11, 2004.

Ulmann M et al: "Ruthnium Carbene-Based Olefin Metathesis Initiators: Catalyst Decomposition and Longevity ", Journal of Organic Chemistry 1999, 64(19), 7202-7207; XP001037574; Sep. 1, 1999.

Ackermann er al: "Ruthenium carbene complexes with imidazolin-2-ylidene ligands allow the formation of tetrasubstituted cycloalkenes by RCM", Tetrahedron Letters 1999, 40(26), 4787-4790; XP004761317; Jun. 25, 1999.

Scholl M et al: "Increased Ring Closing Metathesis Activity of Ruthenium Based Olefin Metathesis Catalysts Coordinated with Imidazolin-2-ylidene Ligands", Tetrahedron Letters 1999, 40(12), 2247-2250; XP004157444; Mar. 19, 1999.

Weskamp et al: "Highly Active Ruthenium Catalysts for Olefin Metathesis: The Synergy of N-Heterocyclic Carbenes and Coordinatively Labile Ligands", Andewandte Chemie International Edition, 1999, 38(16), 2416-2419; XP000984752; vorausveroffentlichit im Internet am Aug. 6, 1999.

H.K.-W. Hui "Thermolysis and Photolysis of 4-Diazo-1,2,3-Triazoles in Benzenoid Solvents, Systems which Reveal Decomposition of Diazo Compounds to Carbenes to Diazo," Tetrahedron Letters, vol. 23 No. 49, 5115-5118; 1982.

M.Begtrup, "Electrophilic and Nucleophilic Substitution in the Trazole N-Oxides and N-MethoxytriazoliumSalts: Preparation of Substituted 1,2,3-Triazoles," J. Chem. Soc., 1, 503-513, 1981.

D. Moderhack et al., "Zur Reaktion von Isocyaniden mit Nitriliminen," Chem. Ber, 1994, 127, 1633-1639.

W.A. Hermann, C. Koecher, Angew. Chem. 1997, 109, 2256-2282.

M. Schuster, S. Blechert, Amgew. Chem. 1997, 2124-2144.

H. Clavier et al., Chem EurJ. 2007.

P. Matthew et al., "1,2,3-Triazolylidnes as Versatile Abnormal Carbene Ligands for Late Transition metals," J. Am. Chem. Soc., Sep. 12, 2008.

J.H. Tales et al., Helcetica Chemica Acta vol. 79 (1996), 61-83.

Tina M. Trnka, et al., "Synthesis and Ativity of Ruthenium Alkylidene Complexes Coordinated with Phosphine and N-Heterocyclic Carbene Ligands," J. Am Chem, Soc. 2003, 125, 2546-2558.

SonBinh TheBao Nguyen; The Designs, Synthesis, and Applications of Well-Defined, Single Component Group VIII Olefin Metathesis Catalysts; Dissertion: California Institute of Technology: 1995.

Eric Lee Kuiokalani Dias; Ruthenium-Based Olefin Metathesis Catalysts: Synthesis, Mechanism, and Activity; Dissertion: California Institute of Technology; 1998.

Karl ofele et al., "Mehrfachbindungen zwischen Hauptgruppenelemente n und Ubergangsmetallen: CXXVI. Heterocyclen-Carbene als phosphananaloge Liganden in Metallkomplexen," J. Organomet. Chem. 459: 177-184 (1993).

Herrmann et al., "Nucleophilic cyclocarbenes as ligands in metal oxides," J. Organomet. Chem. 480: C7-C9 (1994).

Herrmann et al., "Metal Complexes of N-Heterocyclic Carbenes—A New Structural Principle for Catalysts in Homogeneous Catalysts," Agnew. Chem. Int. Ed. Engl. 34(21):p. 2371-2374 (1995).

Herrmann et al., "Chiral Heterocyclic Carbenes in Asymmetric Homoegenous Catalysts," Agnew. Chem. Int. Edn. Engl. 35: 2805-2807 (1996).

Herrmann et al., "Heterocyclic Carbenes" A High-Yielding Synthesis of Novel, Functionalized N-Heterocyclic Carbenes in Liquid Amonia, Chem. Eur. J. 2: 1627-1636 (1996).

Defendant Materia's Inc. Answer and Counterclaims and claims of the University of New Orleans Foundation filed Jun. 3, 2010 in US District Court for the District of Delaware C.A. No. 09-636(NLH-JS).

Defendant Materia, Inc.'s Amended Answer and Counterclaims and Claims of the University of New Orleans Foundation filed Feb. 2, 2011 in US District Court for the District of Delaware C.A. No. 09-636 (NLH-JS).

Decision—Interlocutory Motions Bd.R. 125(b) filed Sep. 26, 2006 in US District Court for the District of Delaware C.A. No. 09-636 (NLH-JS) (Paper No. 72).

Redeclaration—Bd.R. 203(c) filed Sep. 26, 2006 in US District Court for the District of Delaware C.A. No. 09-636 (NLH-JS) (Paper No. 73).

Judgment—Merits—Bd.R. 127 filed Sep. 26, 2006 in US District Court for the District of Delaware C.A. No. 09-636 (NLH-JS) (Paper No. 74).

Minutes of Oral Proceeding Before EPO, Oct. 13, 2008.

Interlocutory Decision, Nov. 26, 2008.

ALKYLIDENE COMPLEXES OF RUTHENIUM CONTAINING N-HETEROCYCLIC CARBENE LIGANDS; USE AS HIGHLY ACTIVE, SELECTIVE CATALYSTS FOR OLEFIN METATHESIS

RELATED APPLICATIONS

This application is a continuation of U.S. patent application Ser. No. 12/875,659, filed Sep. 3, 2010; which is a continuation of U.S. patent application Ser. No. 12/692,229, filed Jan. 22, 2010; which is a continuation of U.S. patent application Ser. No. 11/021,967, filed Dec. 23, 2004, which is a divisional of U.S. patent application Ser. No. 10/630,551, filed Jul. 29, 2003; which is a divisional of U.S. patent application Ser. No. 09/647,742, filed Nov. 27, 2000 now U.S. Pat. No. 6,635,768; which is a National stage of International Application No. PCT/EP99/01785, filed on Mar. 18, 1999; which claims benefit to German Application Number 198 15 275.2, filed Apr. 6, 1998, all of which are incorporated herein by reference in their entirety for all useful purposes.

The invention relates to alkylidene complexes of ruthenium containing N-heterocyclic carbene ligands and a process for preparing olefins by olefin metathesis from acyclic olefins having two or more carbon atoms or/and from cyclic olefins having four or more carbon atoms using at least one of these alkylidene complexes as catalyst.

C—C coupling reactions catalyzed by transition metals are among the most important reactions of organic synthetic chemistry. In this context, olefin metathesis makes a significant contribution, since this reaction enables by-product-free olefins to be synthesized. Olefin metathesis has not only a high potential in the area of preparative, organic synthesis (RCM, ethenolysis, metathesis of acyclic olefins) but also in polymer chemistry (ROMP, ADMET, alkyne polymerization).

Since its discovery in the 1950s, a number of industrial processes have been able to be realized. Nevertheless, olefin metathesis has developed into a broadly applicable synthetic method only recently due to the discovery of new catalysts (J. C. Mol in: B. Cornils, W. A. Het-unarm: Applied Homogeneous Catalysis with Organometallic Compounds, VCH, Weinheim, 1996, p. 318-332; M. Schuster, S. Blechert, Angew. Chem. 1997, 109, 2124-2144; Angew, Chem. Int. Ed. Engl. 1997, 36, 2036-2056).

Numerous, fundamental studies have made important contributions to the understanding of this transition metal-catalyzed reaction in which an exchange of alkylidene units between olefins occurs. The generally accepted mechanism involves metal-alkylidene complexes as active species. These react with olefins to form metallacyclobutane intermediates which undergo cycloreversion to once again form olefins and alkylidene complexes. The isolation of metathesis-active alkylidene and metallacyclobutane complexes supports these mechanistic hypotheses.

Numerous examples may be found, in particular, in the coordination chemistry of molybdenum and tungsten. Specifically the work of Schrock gave well-defined alkylidene complexes whose reactivity can be controlled (J. S. Murdzek, R. R. Schrock, Organometallics 1987, 6, 1373-1374). The introduction of a chiral ligand sphere in these complexes made possible the synthesis of polymers having a high tacticity (K. M. Totland, T. J. Boyd, G. C. Lavoie, W. M. Davis, R. R. Schrock, Macromolecules 1996, 29, 6114-6125). Chiral complexes of the same structural type have also been used successfully in ring-closing metathesis (O. Fujimura, F. J. d. L. Mata, R. H. Grubbs, Organometallics 1996, 15, 1865-1871). However, the high sensitivity toward functional groups, air and water is a drawback.

Recently, phosphine-containing complexes of ruthenium have become established (R. H. Grubbs, S. T. Nguyen, L. K. Johnson, M. A. Hillmyer, G. C. Fu, WO 96/04289, 1994; P. Schwab, M. B. France, J. W. Ziller, R. H. Grubbs, Angew. Chem., 1995, 107, 2119-2181; Angew. Chem. Int. Ed. Engl. 1995, 34, 2039-2041). Owing to the electron-rich, "soft" character of later transition metals, these complexes have a high tolerance toward hard, functional groups. This is demonstrated, for example, by their use in natural product chemistry (RCM of dienes) (Z. Yang, Y. He, D. Vourloumis, H. Vallberg, K. C. Nicolaou, Angew. Chem. 1997, 109, 170-172; Angew. Chem., Int. Ed. Engl. 1997, 36; 166-168; D. Meng, P. Bertinato, A. Balog, D. S. Su, T. Kamenecka, E. J. Sorensen, S. J. Danishefsky, J. Am. Chem. Soc. 1997, 119, 2733-2734; D. Schinzer, A. Limberg, A. Bauer, O. M. Böhm, M. Cordes, Angew. Chem. 1997, 109, 543-544; Angew. Chem., Int. Ed. Engl. 1997, 36, 523-524; A. Fürstner, K. Langemann, J. Am. Chem. Soc. 1997, 119, 9130-9136).

However, the range of variation of the phosphine ligands used is very restricted due to steric and electronic factors. Only strongly basic, bulky alkylphosphines such as tricyclohexylphosphine, triisopropylphosphine and tricyclopentylphosphine are suitable for the metathesis of acyclic olefins and relatively unstrained ring systems. Accordingly, the reactivity of these catalysts cannot be adjusted. Chiral complexes of this structural type have also not been able to be obtained.

For these reasons, it is an object of the invention to develop tailored metathesis catalysts which have a high tolerance toward functional groups as a result of a variable ligand sphere and which allow fine adjustment of the catalyst for specific properties of different olefins.

This object is achieved according to the invention by a complex of ruthenium of the structural formula I,

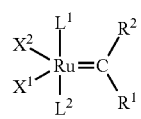

I where $X^1$ and $X^2$ are identical or different and are each an anionic ligand, $R^1$ and $R^2$ are identical or different and can also contain a ring, and $R^1$ and $R^2$ are each hydrogen or/and a hydrocarbon group, where the hydrocarbon groups are identical or different and are selected independently from among straight-chain, branched, cyclic or/and noncyclic radicals from the group consisting of alkyl radicals having from 1 to 50 carbon atoms, alkenyl radicals having from 1 to 50 carbon atoms, alkynyl radicals having from 1 to 50 carbon atoms, aryl radicals having from 1 to 30 carbon atoms and silyl radicals, where one or more of the hydrogen atoms in the hydrocarbon or/and silyl groups can be replaced independently by identical or different alkyl, aryl, alkenyl, alkynyl, metallocenyl, halogen, nitro, nitroso, hydroxy, alkoxy, aryloxy, amino, amido, carboxyl, carbonyl, thio or/and sulfonyl groups, the ligand $L^1$ is an N-heterocyclic carbene of the formulae II-V and the ligand $L^2$ is an uncharged electron donor, in particular an N-heterocyclic carbene of the formulae II-V or an amine, imine, phosphine, phosphite, stibine, arsine, carbonyl compound, carboxyl compound, nitrile, alcohol, ether, thiol or thioether,

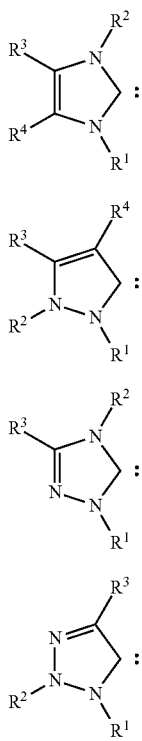

where $R^1$, $R^2$, $R^3$ and $R^4$ the formulae II, III, IV and V are identical or different and are each hydrogen or/and a hydrocarbon group, where the hydrocarbon groups comprise identical or different, cyclic, noncyclic, straight-chain or/and branched radicals selected from the group consisting of alkyl radicals having from 1 to 50 carbon atoms, alkenyl radicals having from 1 to 50 carbon atoms, alkynyl radicals having from 1 to 50 carbon atoms and aryl radicals having from 1 to 30 carbon atoms, in which at least one hydrogen may be replaced by functional groups, and where one or both of $R^3$ and $R^4$ may be identical or different halogen, nitro, nitroso, alkoxy, aryloxy, amido, carboxyl, carbonyl, thio or/and sulfonyl groups.

The alkyl radicals, alkenyl radicals or alkynyl radicals in the formulae I to V preferably have from 1 to 20 carbon atoms, particularly preferably from 1 to 12 carbon atoms.

Figure 1:
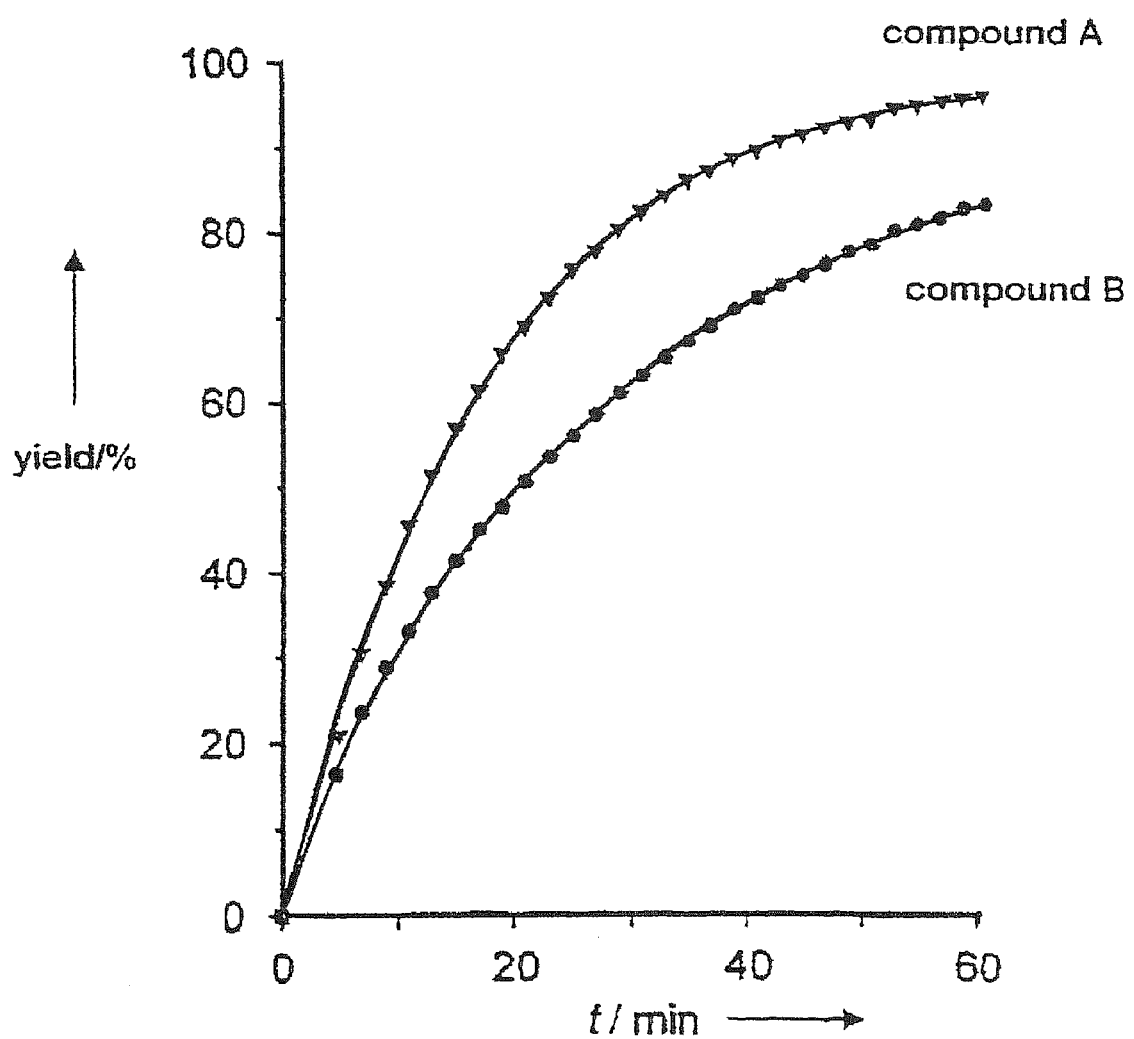
FIG. 1 illustrates the yield % versus t/min for compounds A and B in a ring-opening metathesis polymerization of 1,5-cyclooctadiene
Figure 2:
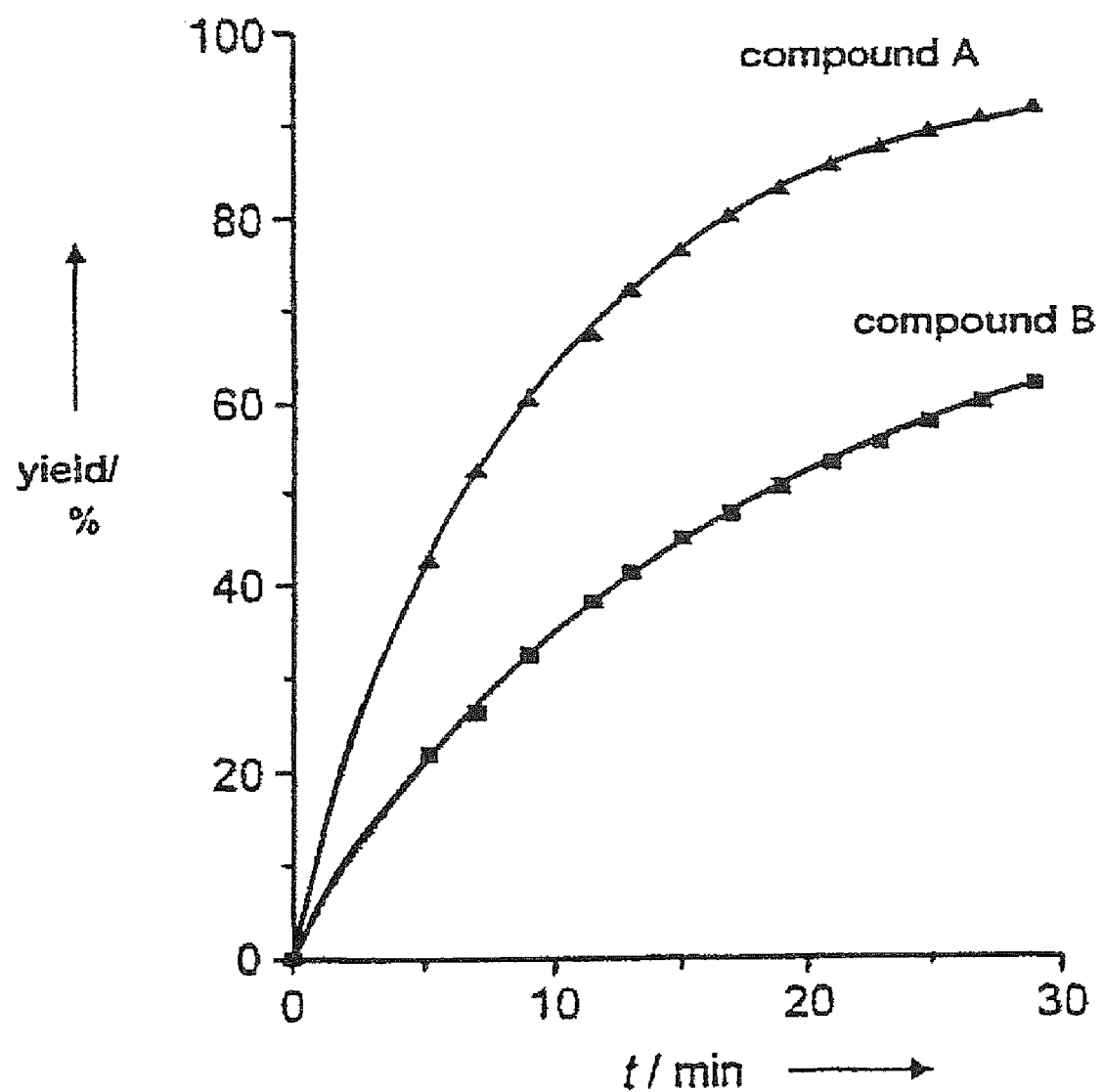
FIG. 2 illustrates the yield % versus t/min for compounds A and B in a ring-opening metathesis polymerization of cyclooctene.

The complexes of the invention are highly active catalysts for olefin metathesis. They are particularly inexpensive. In olefin metathesis, the catalysts of the invention display not only a high tolerance toward a variety of functional groups but also a wide range of possible variations in the ligand sphere. Variation of the preparatively readily obtainable N-heterocyclic carbene ligands enables activity and selectivity to be controlled in a targeted manner and, in addition, chirality can be introduced in a simple way.

The anionic ligands $X^1$ and $X^2$ of the complex of the of invention, which are identical or different, are preferably each halide, pseudohalide, tetraphenylborate, perhalogenated, tetraphenylborate, tetrahaloborate, hexahalophosphate, hexahaloantimonate, trihalomethanesulfonate, alkoxide, carboxylate, tetrahaloaluminate, tetracarbonylcobaltate, hexahaloferrate (III), tetrahaloferrate (III) or/and tetrahalopalladate (II), with preference being given to halide, pseudohalide, tetraphenylborate, perfluorinated tetraphenylborate, tetrafluoroborate, hexafluorophosphate, hexafluoroantimonate, trifluorotnethanesulfonate, alkoxide, carboxylate, tetrachloroaluminate, tetracarbonylcobaltate, hexafluoroferrate (III) tetrachloroferrate (III) or/and tetrachloropalladate (II) and preferred pseudohalides being cyanide, thiocyanate, cyanate, isocyanate and isothiocyanate.

In the formulae II, III, IV and V, some or all of the hydrogen in the hydrocarbon groups $R^1$, $R^2$, $R^3$ and $R^4$ can be replaced independently by identical or different halogen, nitro, nitroso, hydroxy, alkoxy, aryloxy, amino, amido, carboxyl, carbonyl, thio, sulfonyl or/and metallocenyl groups. In these formulae, $R^3$ and $R^4$ can form a fused-on ring system.

The ligands $L^1$ and $L^2$ of the complex of the structural formula I can form a chelating ligand of the formula VI $$L^2\text{-}Y\text{-}L^2 \qquad \text{VI}$$

where the bridges Y can comprise cyclic, noncyclic, straight-chain or/and branched radicals selected from the group consisting of alkylene radicals having from 1 to 50 carbon atoms, alkenylene radicals having from 1 to 50 carbon atoms, alkynylene radicals having from 1 to 50 carbon atoms, arylene radicals having from 1 to 30 carbon atoms, metallocenylene, borylene and silylene radicals in which one or more hydrogens may be replaced independently by identical or different alkyl, aryl, alkenyl, alkynyl, metallocenyl, halo, nitro, nitroso, hydroxy, alkoxy, aryloxy, amino, amido, carboxyl, carbonyl, thio or/and sulfonyl groups, preferably alkyl, aryl or/and metallocenyl groups.

The ligands of the formulae II, III, IV, V or/and VI can have central, axial or/and planar chirality.

In the structural formula I of the complex, $R^1$ and $R^2$ are preferably hydrogen, substituted or/and unsubstituted alkyl, alkenyl or/and aryl radicals, $X^1$ and $X^2$ are preferably halide, alkoxide or/and carboxylate ions and $L^1$ and $L^2$ are preferably each an N-heterocyclic carbene of the formula II.

The complexes are usually synthesized by ligand replacement in corresponding phosphine complexes. Two phosphine ligands can be replaced selectively in accordance with the reaction equation (1) or only one can be replaced in accordance with reaction equation (2). In the case of single replacement, the second phosphine can be replaced selectively by another electron donor, e.g. pyridine, phosphine, N-heterocyclic carbene, phosphite, stilbene, arsine, in accordance with reaction equation (3).

In particular, this route makes it possible for the first time to prepare chiral, metathesis-active catalysts based on ruthenium (example complexes 2 and 3).

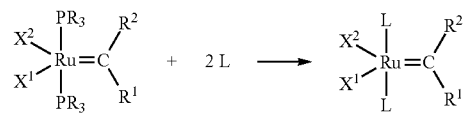

-continued

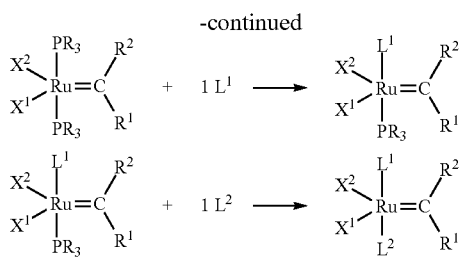

The complexes of the invention are found to be extremely efficient catalysts in olefin metathesis. The excellent metathesis activity is demonstrated in the examples by means of a number of examples of different metathesis reactions.

The present invention therefore also encompasses processes for all olefin metathesis reactions such as ring-opening metathesis polymerization (ROMP), metathesis of acyclic olefins, ethenolysis, ring-closing metathesis (RCM), acyclic diene metathesis polymerization (ADMET) and depolymerization of olefin polymers. The high stability and tolerance of the complexes of the invention toward functional groups; in particular alcohol, amine, thiol, ketone, aldehyde, carboxylic acid, ester, amide, ether, silane, sulfide and halogen groups, makes it possible for such functional groups to be present during the metathesis reaction.

The object of the invention is also achieved by a process for preparing acyclic olefins having two or more carbon atoms or/and cyclic olefins having four or more carbon atoms, in each case of the formula VII

VII

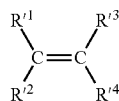

from acyclic olefins having two or more carbon atoms or/and from cyclic olefins having four or more carbon atoms, in each case corresponding to the formula VII by an olefin metathesis reaction in the presence of at least one catalyst, wherein
a catalyst as claimed in any one of claims 1 to 7 is used and $R'^1$, $R'^2$, $R'^3$ and $R'^4$ in the formula VII are hydrogen or/and hydrocarbon groups,
where the hydrocarbon group is each selected independently from among straight-chain, branched, cyclic or/and non-cyclic radicals of the group consisting of alkyl radicals having from 1 to 50 carbon atoms, alkenyl radicals having from 1 to 50 carbon atoms, alkynyl radicals having from 1 to 50 carbon atoms, aryl radicals having from 1 to 30 carbon atoms, metallocenyl or/and silyl radicals, in which one or more hydrogens may be replaced by a functional group,
where one or more of $R'^1$, $R'^2$, $R'^3$ and $R'^4$ may independently be identical or different halogen, nitro, nitroso, hydroxy, alkoxy, aryloxy, amino, amido, carboxyl, carbonyl, thio, sulfonyl or/and metallocenyl groups.

The olefins used preferably contain one or more double bonds. In particular, $R'^1$, $R'^2$, $R'^3$ and $R'^4$ in the olefins of the formula VII to be prepared form, in pairs, one or more identical or different rings.

Preferably, some or all of the hydrogen atoms in the hydrocarbon groups $R'^1$, $R'^2$, $R'^3$ and $R'^4$ of the olefins of the formula VII to be prepared are replaced independently by identical or different halogen, silyl, nitro, nitroso, hydroxy, alkoxy, aryloxy, amino, amido, carboxyl, carbonyl, thio, sulfonyl or/and metallocenyl groups.

The process of the invention can be carried out in the presence or absence of solvents, but preferably in the presence of organic solvents. The process of the invention can advantageously be carried out with addition of a Brönsted acid, preferably HCl, HBr, HI, $HBF_4$, $HPF_6$ or/and trifluoroacetic acid, or/and with addition of a Lewis acid, preferably $BF_3$, $AlCl_3$ or/and $ZnI_2$.

Surprisingly, this makes it possible for the first time to tailor a wide variety of olefins individually to different properties on the basis of small variations in the catalysis conditions or/and the catalysts, since the process of the invention for preparing olefins has an unexpectedly high tolerance toward functional groups.

EXAMPLES

The following examples illustrate the invention but do not restrict its scope.

1) Preparation of the Complex of the Invention

General Procedure:
1 mmol of $(PPh_3)_2Cl_2Ru(=CHPh)$ was dissolved in 20 ml of toluene and admixed with a solution of 2.2 equivalents of the appropriate imidazolin-2-ylidene in 5 ml of toluene. The reaction solution was stirred at room temperature RT for 45 minutes, subsequently evaporated to about 2 ml and the crude product was precipitated using 25 ml of pentane. The crude product was taken up in 2 ml of toluene and precipitated using 25 ml of pentane a number of times. The residue was extracted with toluene, the solution was evaporated to dryness, washed twice with pentane and dried for a number of hours in a high vacuum.

The data from low-temperature NMR spectra are mostly reported for characterization, since the spectra at room temperature sometimes did not give all the information because of dynamic effects.

The following compounds are prepared by the above-described general procedure:

1a) Benzylidenedichlorobis(1,3-diisopropylimidazolin-2-ylidene)ruthenium

Complex 1:
Yield: 487 mg (0.86 mmol=86% of theory)
Elemental analysis EA for $C_{25}H_{38}Cl_2N_4Ru$ (566.58):
found C, 53.21; H, 6.83; N, 9.94.
calculated C, 53.00; H, 6.76; N, 9.89.
$^1$H-NMR ($CD_2Cl_2$/200K): δ 20.33 (1H, s, Ru=CH), 8.25 (2H, d, $^3J_{HH}$=7.6 Hz, o-H of $C_6H_5$) 7.63 (1H, t, $^3J_{HH}$=7.6 Hz, p-H of $C_6H_5$), 7.34 (2H, t, m-H of $C_6H_5$, $^3J_{HH}$=7.6 Hz), 7.15 (2H, br, NCH), 7.03 (2H, br, NCH), 5.97 (2H, spt, $^3J_{HH}$=6.4 Hz, NCHMe$_2$), 3.73 (2H, spt, $^3J_{HH}$=6.4 Hz, NCHMe$_2$), 1.64 (12H, d, $^3J_{HH}$=6.4 Hz, NCHMe$_2$), 1.11 (6H, d, $^3J_{HH}$=6.4 Hz, NCHMe$_2$), 0.75 (6H, d, $^3J_{HH}$=6.4 Hz, NCHMe$_2$).
$^{13}$C—NMR ($CD_2Cl_2$/200 K): δ 295.6 (Ru=CH), 183.5 (NCN), 151.6 (ipso-C of $C_6H_5$), 129.5, 128.6 and 128.1 (o-C, m-C and p-C of $C_6H_5$), 118.1 and 117.2 (NCH), 52.1 and 50.1 (NCHMe$_2$), 24.5, 23.8, 23.8 and 22.4 (NCHMe$_2$).

1b) Benzylidenedichlorobis(1,3-di((R)-1'-phenylethyl)-imidazolin-2-ylidene)ruthenium Complex 2:
Yield: 676 mg (0.83 mmol=83% of theory)
EA for $C_{45}H_{46}Cl_2N_4Ru$ (814.86)

found C, 66.48; H, 5.90; N, 6.73. calc. C, 66.33; H, 5.69; N, 6.88.

$^1$H-NMR (CD$_2$Cl$_2$/200K): δ 20.26 (1H, s, Ru=CH), 8.13 (2H, br, o-H C$_6$H$_5$), 7.78-6.67 (29H, of which 2m-H and 1p-H of C$_6$H$_5$, 20H of NCHMePh, 2H of NCHMePh and 4H of NCH), 4.91 (2H, m, NCHMePh), 1.84 (3H, d, $^3J_{HH}$=6.6 Hz, NCHMePh), 1.81 (3H, d, $^3J_{HH}$=6.6 Hz, NCHMePh), 1.51 (3H, d, $^3J_{HH}$=6.6 Hz, NCHMePh), 1.21 (3H, d, $^3J_{HH}$=6.6 Hz, NCHMePh).

$^{13}$C-NMR (CD$_2$C$_2$/200K): δ 294.7 (Ru=CH), 186.0 and 185.6 (NCN), 151.2 (ipso-C of C$_6$H$_5$), 141.2, 140.3, 140.1 and 139.9 (ipso-C of NCHMePh), 133.1-125.9 (o-C, m-C, p-C of C$_6$H$_5$ and NCHMePh), 120.5, 119.9, 119.2 and 118.8 (NCH), 57.6, 57.4, 56.7 and 56.1 (NCHMePh), 22.2, 20.6, 20.4 and 20.3 (NCHMePh).

1c) Benzylidenedichlorobis(1,3-di-((R)-1'-naphthylethyl)imidazolin-2-ylidene)ruthenium Complex 3:
Yield: 792 mg (0.78 mmol=78% of theory)
EA for C$_{61}$H$_{54}$Cl$_2$N$_4$Ru (1015.1):
found C, 72.34; H, 5.46; N, 5.45.
calc. C, 72.18; H, 5.36; N, 5.52.

$^1$H-NMR (CD$_2$Cl$_2$/260K): δ 20.90 (1H, s, Ru=CH), 8.99 (2H, br, o-H of C$_6$H$_5$), 8.2-5.6 (39H, of which 2m-H and 1p-H of C$_6$H$_5$, 28H of NCHMeNaph, 4H of NCH and 4H of NCH-MeNaph), 2.5-0.8 (12H, m, NCHMeNaph).

$^{13}$C-NMR (CD$_2$Cl$_2$/260K): δ 299.9 (Ru=CH), 187.2 and 184.7 (NCN), 152.0 (ipso-C of C$_6$H$_5$), 136.0-124.0 (o-C, m-C, p-C of C$_6$H$_5$ and NCHMeNaph), 121.7, 121.0, 119.9, and 118.9 (NCH), 56.7, 56.1, 55.0 and 54.7 (NCHMeNaph), 24.7, 24.3, 21.0 and 20.0 (NCHMeNaph).

For the following complexes, slight deviations from the general procedure are necessary:

1d) (4-Chlorobenzylidene)dichlorobis(1,3-diisopropylimidazolin-2-ylidene)ruthenium Complex 4:
1 mmol of (PPh$_3$)$_2$Cl$_2$Ru[=CH (p-C$_6$H$_4$Cl)] was used as starting material. The further procedure corresponded to the abovedescribed general procedure.
Yield: 535 mg (0.89 mmol=89% of theory)
EA for C$_{24}$H$_{38}$Cl$_3$N$_4$Ru (601.03):
found C, 48.13; H, 6.33; N, 9.24.
calc. C, 47.96; H, 6.37; N, 9.32.

$^1$H-NMR (CD$_2$Cl$_2$/200 K): δ 20.33 (1H, s, Ru=CH), 8.25 (2H, d, $^3J_{HH}$=7.6 Hz, o-H of C$_6$H$_4$Cl), 7.63 (1H, t, $^3J_{HH}$=7.6 Hz, m-H of C$_6$H$_4$Cl), 7.15 (2H, br, NCH), 7.03 (2H, br, NCH), 5.97 (2H, spt, $^3J_{HH}$=6.4 Hz, NCHMe$_2$), 3.73 (2H, spt, $^3J_{HH}$=6.4 Hz, NCHMe$_2$), 1.64 (12H, d, $^3J_{HH}$=6.4 Hz, NCHMe$_2$), 1.11 (6H, d, $^3J_{HH}$=6.4 Hz, NCHMe$_2$), 0.75 (6H, d, $^3J_{HH}$=6.4 Hz, NCHMe$_2$).

$^{13}$C-NMR (CD$_2$Cl$_2$/200 K): δ 295.6 (Ru=CH), 183.5 (NCN), 151.6 (ipso-C of C$_6$H$_4$Cl), 134.3 (p-C of C$_6$H$_4$Cl), 128.6 and 128.1 (o-C and m-C of C$_6$H$_4$Cl), 118.1 and 117.2 (NCH), 52.1 and 50.1 (NCHMe$_2$), 24.5, 23.8, 23.8 and 22.4 (NCHMe$_2$).

1e) Benzylidenedichlorobis(1,3-dicyclohexylimidazolin-2-ylidene)ruthenium

Complex 5:
1 mmol of (PPh$_3$)$_2$Cl$_2$Ru(=CHPh) was dissolved in 25 ml of toluene and admixed with a solution of 2.2 equivalents of 1,3-dicyclohexylimidazolin-2-ylidene in 5 ml of toluene. The reaction solution was stirred at RT for 45 minutes and subsequently freed of the solvent. Unlike the general procedure, the crude product was purified by flash chromatography.
Yield: 305 mg (0.42 mmol=42% of theory).
EA for C$_{37}$H$_{54}$Cl$_2$N$_4$Ru (726.84):
found C, 61.23; H, 7.56; N, 7.87.
calc. C, 61.14; H, 7.49; N, 7.71.

$^1$H-NMR (CD$_2$Cl$_2$/298 K): δ 20.45 (1H, s, Ru=CH), 8.31 (2H, d, $^3J_{HH}$=7.6 Hz, o-H— of C$_6$H$_5$), 7.63 (1H, t, $^3J_{HH}$=7.6 Hz, p-H— of C$_6$H$_5$), 7.34 (2H, t, $^3J_{HH}$=7.6 Hz, m-H— of C$_6$H$_5$), 7.14 (2H, br, NCH), 7.00 (2H, br, NCH), 6.06 (2H, br, CH of NC$_6$H$_{11}$), 3.82 (2H, br, CH of NC$_6$H$_{11}$), 1.64 (12H, br, CH$_2$ of NC$_6$H$_{11}$), 0.93 (12H, br, CH$_2$ of NC$_6$H$_{11}$).

$^{13}$C-NMR (CD$_2$Cl$_2$/298 K): δ 299.4 (Ru=CH), 182.9 (NCN), 152.0 (ipso-C of C$_6$H$_5$), 131.1, 129.8 and 129.1 (o-C, m-C and p-C of C$_6$H$_5$), 118.3 and 117.8 (br, NCH), 59.6 and 57.5 (br, CH of NC$_6$H$_{11}$), 35.7, 26.9 and 25.6 (br, CH$_2$ of NC$_6$H$_{11}$)

1f) Benzylidenedichloro(1,3-di-tert-butylimidazolin-2-ylidene) (triphenylphosphine)ruthenium Complex 6:
1 mmol of (PPh$_3$)$_2$Cl$_2$Ru(=CHPh) was dissolved in 20 ml of toluene and admixed with a solution of 1.1 equivalents of 1,3-di-tert-butylimidazolin-2-ylidene in 5 ml of toluene. The reaction solution was stirred at RT for 30 minutes, subsequently evaporated to about 2 ml and the crude product was precipitated using 25 ml of pentane. The further work-up was carried out as described in the general procedure.
Yield; 493 mg (0.70 mmol=70% of theory)
EA for C$_{36}$H$_{41}$Cl$_2$N$_2$P$_1$Ru (704.69):
found C, 61.12; H, 5.55; N, 3.62; P, 4.59.
calc. C, 61.36; H, 5.86; N, 3.98; P, 4.38.

$^1$H-NMR (CD$_2$Cl$_2$/200 K): δ 20.70 (1H, s, Ru=CH), 8.03 (2H, d, $^3J_{HH}$=7.6 Hz, of C$_6$H$_5$), 7.50-6.95 (20H, of which 2m-H and 1p-H of C$_6$H$_5$, 15H of PPh$_3$ and 2H of NCH), 1.86 (9H, s, NCMe$_3$), 1.45 (9H, s, NCMe$_3$).

$^{13}$C-NMR (CD$_2$Cl$_2$/200 K): δ 307.4 (br, Ru=CH), 178.3 (d, J$_{PC}$=86 Hz, NCN), 151.5 (d, J$_{PC}$=4.5 Hz, ipso-C of C$_6$H$_5$), 135.0 (m, o-C of PPh$_3$), 131.9 (m, ipso-C of PPh$_3$), 130.2 (s, p-C of PPh$_3$), 129.5, 128.6 and 128.1 (s, o-C, m-C and p-C of C$_6$H$_5$), 128.0 (m, m-C of PPh$_3$), 117.7 and 117.6 (NCH), 58.7 and 58.5 (NCMe$_3$), 30.0 and 29.5 (NCMe$_3$).

$^{31}$P-NMR (CD$_2$Cl$_2$/200 K): δ 40.7 (s, PPh$_3$).

1 g) Benzylidenedichloro-(1,3-dicyclohexylimidazolin-2-ylidene)(tricyclohexylphosphine)ruthenium

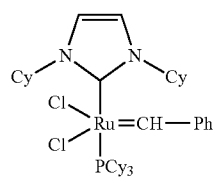

A solution of 1.2 mmol of dicyclohexylimidazolin-2-ylidene is added dropwise at −78° C. to 1 mmol of RuCl$_2$(PCy$_3$)$_2$(CHPh) in 100 ml of THF. The mixture is slowly warmed to room temperature over a period of 5 hours and the solvent is subsequently removed. The crude product is extracted with a mixture of 2 ml of toluene and 25 ml of pentane and the product is precipitated from this solution at −78° C.

Yield: 0.80 mmol (80% of theory)

EA for $C_{40}H_{63}Cl_2N_2PRu$:

found C, 61.99; H, 8.20; N, 3.62. calc. C, 61.11; H, 8.29; N, 3.59.

$^1$H NMR (CD$_2$Cl$_2$/25° C.): δ=20.30 (1H, d, $^3J_{PH}$=7.4 Hz, Ru=CH), 8.33 (2H, d, $^3J_{HH}$=7.4 Hz, o-H of C$_6$H$_5$), 7.62 (1H, t, $^3J_{HH}$=7.4 Hz, p-H of C$_6$H$_5$), 7.33 (2H, t, $^3J_{HH}$=7.4 H$_2$, o-H of C$_6$H$_5$), 7.11 (1H, s, NCH), 6.92 (1H, s, NCH), 5.97 (1H, m, CH of NC$_6$H$_{11}$), 3.36 (1H, m, CH of NC$_6$H$_{11}$), 2.42 (3H, m, CH of PCy$_3$), 1.90-0.89 (50H, all m, CH$_2$ of NC$_6$H$_{11}$ and PCy$_3$).

$^{13}$C NMR (CD$_2$Cl$_2$/25° C.): d=298.7 (Ru=CH), 181.2 (d, $J_{PC}$=88 Hz, NCN), 152.5 (ipso-C of C$_5$H$_5$), 130.8, 129.8, and 129.2 (o-C, m-C, and p-C of C$_6$H$_5$), 118.9 and 118.0 (NCH), 59.5 and 57.7 (CH of NC$_5$H$_{11}$) 33.2 (d, $J_{PC}$=17 Hz, ipso-C of PCy$_3$), 29.9 (s, m-C of PCy$_3$), 26.8 (d, $J_{PC}$=3.7 Hz, o-C of PCy$_3$), 25.4 (s, p-C of PCy$_3$) 34.9, 33.3, 33.1, 28.2, 28.1, and 25.7 (CH$_2$ of NC$_6$H$_{11}$).

$^{31}$P NMR (CD$_2$Cl$_2$/25° C.) d=28.2.

1 h) Benzylidenedichloro(1,3-di-((R)-1'-phenyl-ethyl)-imidazolin-2-ylidene)(tricyclohexylphos-phine)ruthenium

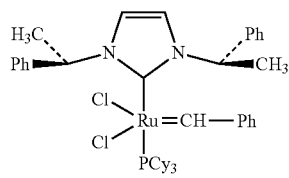

A solution of 1.2 mmol of di-(R)-1'-phenylethylimidazo-lin-2-ylidene is added dropwise at −78° C. to 1 mmol of RuCl$_2$(PCy$_3$)$_2$(CHPh) in 100 ml of THF. The mixture is slowly warmed to room temperature over a period of 5 hours and the solvent is subsequently removed. The crude product is extracted with a mixture of 2 ml of toluene and 25 ml of pentane and the product is precipitated from this solution at −78° C.

Yield: 0.74 mmol (74% of theory)

EA for $C_{44}H_{59}Cl_2N_2PRu$:

calc. C, 64.53; H, 7.27; N, 3.42. found C, 64.58; H, 7.34; N, 3.44.

$^1$H NMR (CD$_2$Cl$_2$/25° C.): d 20.19 (1H, d, $^3J_{PH}$=4.5 Hz, Ru=CH), 7.74-7.00 (15H, all m, CH of C$_6$H$_5$), (1H, m, NCHMePh), 6.73 (1H, s, NCH), 6.70 (1H, s, NCH), 2.52 (1H, m, NCHMePh), 2.44 (3H, m, CH of PCy$_3$), 2.11 (3H, d, $^3J_{HH}$=6.8 Hz, NCHMePh), 1.82-1.12 (30H, all m, CH$_2$ of PCy$_3$) 1.35 (3H, d, $^3J_{HH}$=6.8 Hz, NCHMePh).

$^{13}$C NMR (CD$_2$Cl$_2$/25° C.): δ=292.7 (Ru=CH), 183.4 (d, $J_{PC}$=78 Hz, NCN), 151.8 (ipso-C of C$_6$H$_5$), 140.1 and 139.5 (ipso-C of NCHMEPh), 129.5, 128.5, 128.3, 127.9, 127.5, 127.4, 127.2, 126.6, and 126.1 (o-C, m-C and p-C of C$_6$H$_5$) 119.8 and 118.4 (NCH), 57.4 and 56.2 (NCHMePh), 31.3 (d, $J_{PC}$=17 Hz, ipso-C of PCy$_3$), 29.0 (s, m-C of PCy$_3$), 28.9 (s, m-C of PCy$_3$), 27.2 (d, $J_{PC}$=3.7 Hz, o-C of PCy$_3$), 27.0 (d, $J_{PC}$=3.7 Hz, o-C of PCy$_3$), 25.8 (s, p-C of PCy$_3$) 21.7 and 20.3 (NCHMePh).

$^{31}$P NMR (CD$_2$Cl$_2$/25° C.): δ 38.1.

1i) Benzylidenedichloro(1,3-di-((R)-1'-naphthyl-ethyl)-imidazolin-2-ylidene)(tricyclohexylphos-phine)ruthenium

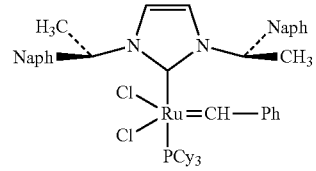

A solution of 1.2 mmol of di-(R)-1'-naphthylethylimida-zolin-2-ylidene is added dropwise at −78° C. to 1 mmol of RuCl$_2$(PCy$_3$)$_2$(CHPh) in 100 ml of THF. The mixture is slowly warmed to room temperature over a period of 5 hours and the solvent is subsequently removed. The crude product is extracted with a mixture of 2 ml of toluene and 25 ml of pentane and the product is precipitated from this solution at −78° C.

Yield: 0.72 mmol (72% of theory)

EA for $C_{52}H_{63}Cl_2N_2PRu$:

calc. C, 67.95; H, 6.91; N, 3.05. found C, 68.09; H, 7.02; N, 3.04.

$^1$H NMR (CD$_2$Cl$_2$/25° C.): δ 20.33 (1H, d, $^3J_{HH}$=5.4 Hz, Ru=CH), 8.88 (2H, d, $^3J_{HH}$=8.0 Hz, o-H of C$_6$H$_5$) 7.94-6.96 (17H, all m, CH of C$_6$H$_5$), 6.70 (1H, s, NCH), 6.61 (1H, s, NCH), 5.83 (1H, m, NCHMeNaph), 2.59 (1H, m, NCHMeNaph), 2.49 (3H, m, CH of PCy$_3$), 2.44 (3H, d, $^3J_{HH}$=6.8 Hz, NCHMeNaph), 1.95-1.01 (30H, all m, CH$_2$ of PCy$_3$) 1.54 (3H, d, $^3J_{HH}$=6.8 Hz, NCHMeNaph).

$^{13}$C NMR (CD$_2$Cl$_2$/25° C.): δ=298.4 (Ru=CH), 184.0 (d, $J_{PC}$=87 Hz, NCN), 152.3 (ipso-C of C$_6$H$_5$), 138.3 and 137.6 (ipso-C of NCHMeNaph), 134.3-122.9 (o-C, m-C, and p-C of C$_6$H$_5$, CHMeNaph) 120.6 and 119.5 (NCH), 56.4 and 55.7 (NCHMeNaph), 32.5 (d, $J_{PC}$=17 Hz, ipso-C of PCy$_2$), 30.1 (s, m-C of PCy$_2$), 30.0 (s, m-C of PCy$_2$), 28.1 (pseudo-t, $J_{PC}$=7.4 Hz, o-C of PCy$_3$), 26.8 (s, p-C of PCy$_3$) 24.0 and 22.7 (NCHMeNaph).

$^{31}$P NMR (CD$_2$Cl$_2$/25° C.): δ=31.8.

2) Use of the Complex of the Invention in Olefin Metathesis

The following examples demonstrate the potential of the complexes of the invention in olefin metathesis. The advantage of these complexes of the invention compared to phosphine-containing complexes is the targeted and inexpensive variation of the radicals R on the nitrogen atoms of the N-heterocyclic, carbene ligands. This tailoring of the catalysts of the invention on the basis of individual properties of the olefins to be subjected to metathesis enables both activity and selectivity of the reaction to be controlled.

2a) Ring-Opening Metathesis Polymerization (ROMP)

Norbornene, cyclooctene and functionalized norbornene derivatives serve as examples.

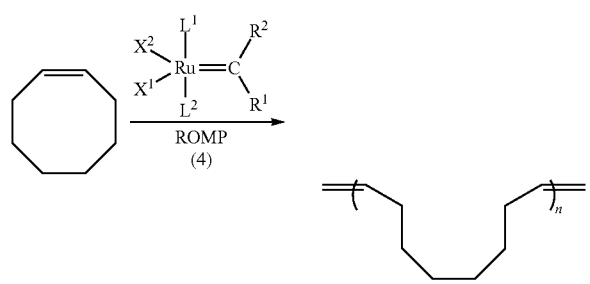

Typical Reaction Procedure for the Polymerization of Cyclooctene (or Norbornene):

410 μl (3.13 mmol) of cyclooctene were added to a solution of 3.6 mg (6.3 μmol) of 1 in 0.5 ml of methylene chloride. After about 10 minutes, a highly viscous gel which could no longer be stirred had formed. 1 ml of methylene chloride was added. This procedure was repeated whenever the stirrer was no longer able to operate (a total of 3 ml of methylene chloride). After 1 hour, 5 ml of methylene chloride to which small amounts of tert-butyl ether and 2,6-di-tert-butyl-4-methylphenol had been added were introduced. After a further 10 minutes, the solution was slowly added dropwise to a large excess of methanol, the mixture was filtered and the solid was dried in a high vacuum for a number of hours.

Yield: 291 mg (2.64 mmol=84.3% of theory)

TABLE 1

Polymerization of norbornene and cyclooctene

| Example | Complex | Monomer | Ratio of [monomer]/[cat.] | Reaction time t | Yield |
|---|---|---|---|---|---|
| 2.1a | 1 | Norbornene | 100:1 | 1 min | 91% |
| 2.1b | 5 | Norbornene | 100:1 | 1 min | 92% |
| 2.1c | 1 | Cyclooctene | 500:1 | 1 h | 84% |
| 2.1d | 1 | Cyclooctene | 500:1 | 2 h | 97% |
| 2.1e | 5 | Cyclooctene | 500:1 | 1 h | 87% |

Typical Reaction Procedure for the Polymerization of Functionalized Norbornene Derivatives:

The formula VIII shows the basic skeleton of the norbornene derivatives used in Table 2.

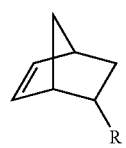

VIII 0.3 ml of a solution of 432 mg (3.13 mmol) of 5-carboxyl-2-norbornene (formula VIII with R=CO$_2$H) in methylene chloride was added to a solution of 3.6 mg (6.3 μmol) of 1 in 0.2 ml of methylene chloride. After about 10 minutes, a highly viscous gel which could no longer be stirred had formed. A further 0.5 ml of methylene chloride was added. This procedure was repeated whenever the stirrer was no longer able to operate. After 1 hour, 5 ml of methylene chloride to which small amounts of tert-butyl ether and 2,6-di-tert-butyl-4-methylphenol had been added were introduced. After a further 10 minutes, the solution was slowly added dropwise to a large excess of methanol, filtered and the solid was dried in a high vacuum for a number of hours.

Yield: 423 mg (3.06 mmol=98.1% of theory)

The reactions at 50° C. were carried out in an analogous manner in dichloroethane instead of methylene chloride.

TABLE 2

Polymerization of functionalized norbornene derivatives

| Example | Complex | Radical R in formula VIII | T[° C.] | Reaction time t | Yield |
|---|---|---|---|---|---|
| 2.1f | 1 | O$_2$CCH$_3$ | 25 | 30 min | 99% |
| 2.1g | 1 | CH$_2$OH | 25 | 2 h | 15% |
| 2.1h | 1 | CH$_2$OH | 50 | 2 h | 18% |
| 2.1i | 1 | CHO | 25 | 2 h | 36% |
| 2.1k | 1 | CHO | 50 | 2 h | 52% |
| 2.1l | 1 | COCH$_3$ | 25 | 2 h | 42% |
| 2.1m | 1 | COCH$_3$ | 50 | 2 h | 67% |
| 2.1n | 1 | CO$_2$H | 25 | 2 h | 98% |

The polymerization of norbornene occurred in seconds. In the polymerization of cyclooctene, virtually quantitative conversions were obtained within one hour (Table 1). Differences in activity can be detected by use of various complexes under dilute conditions and demonstrate the dependence of the activity on the substitution pattern of the carbene ligands used. The high stability and tolerance toward functional groups is demonstrated by the polymerization of functionalized norbornene derivatives containing ester, alcohol, aldehyde, ketone or/and carboxylic acid groups (Table 2). Here, monomers of the formula VIII with R=CH$_2$OH, CHO and CO$_2$H were able to be polymerized for the first time.

2.2) Ring-Closing Metathesis (RCM) of 1,7-octadiene

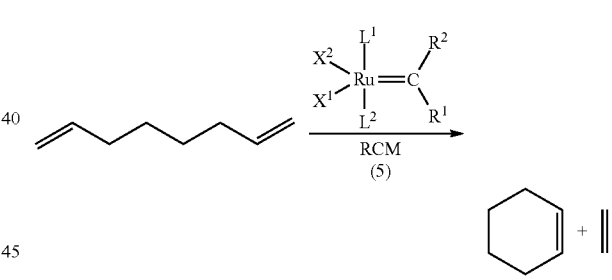

Typical Reaction Procedure for RCM of 1,7-octadiene:

A solution of 3.6 mg (6.3 μmol) of 1 in 2 ml of dichloroethane was admixed with 46 μl (0.31 mmol) of 1,7-octadiene, and the reaction mixture was placed in an oil bath at 60° C. After one hour, the reaction mixture was analyzed by GC/MS.

TABLE 3

RCM of 1,7-octadiene (octadiene/catalyst = 50:1)

| Example | Complex | Solvent | T[° C.] | Reaction time t | Yield |
|---|---|---|---|---|---|
| 2.2a | 1 | Methylene chloride | 25 | 5.5 h | 51% |
| 2.2b | 1 | Methylene chloride | 25 | 24 h | 70% |
| 2.2c | 1 | Dichloroethane | 60 | 1 h | 99% |
| 2.2d | 2 | Dichloroethane | 60 | 1 h | 99% |
| 2.2e | 3 | Dichloroethane | 60 | 1 h | 99% |
| 2.2f | 5 | Dichloroethane | 60 | 1 h | 99% |

The potential in ring-closing metathesis was illustrated by the reaction of 1,7-octadiene to form cyclohexene with liberation of ethylene (Table 3). 1 gave a yield of 51% after 5.5 hours; at 60° C., all complexes of the invention used gave quantitative conversions.

2.3) Metathesis of Acyclic Olefins

A) Metathesis of 1-octene:

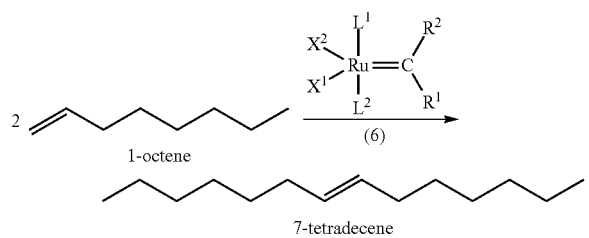

Typical Reaction Procedure for the Metathesis of 1-octane:

A solution of 3.6 mg (6.3 µmol) of 1 in 2 ml of dichloroethane was admixed with 49 µl (0.31 mmol) of 1-octene, and the reaction mixture was placed in an oil bath at 60° C. After 3 hours, the reaction mixture was analyzed by GC/MS.

TABLE 4

Homometathesis of 1-octene (octene/catalyst = 50:1)

| Example | Complex | T[° C.] | Reaction time t | Conversion of 1-octene | Selectivity[a] |
|---|---|---|---|---|---|
| 2.3a | 2 | 60 | 1 h | 31% | 98% |
| 2.3b | 2 | 60 | 2 h | 58% | 97% |
| 2.3c | 1 | 60 | 1 h | 83% | 73% |
| 2.3d | 1 | 60 | 3 h | 97% | 63% |

[a]The selectivity indicates the proportion of 7-tetradecene compared to other metathesis products B) Metathesis of Methyl Oleate:

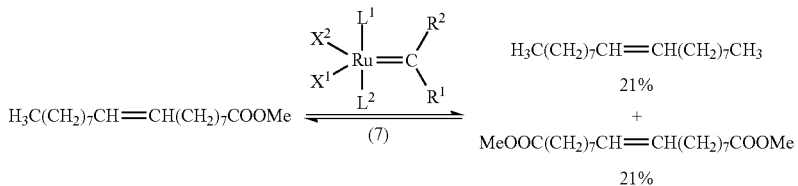

Typical Reaction Procedure for the Metathesis of Methyl Oleate:

A solution of 3.6 mg (6.3 µmol) of 1 in 0.5 ml of dichloroethane was admixed with 1.06 ml (3.13 mmol) of methyl oleate, and the reaction mixture was placed in an oil bath at 60° C. for 15 hours. GC/MS analysis indicated the equilibrium of metathesis products shown in the reaction equation (7).

The metathesis of terminal and internal olefins was demonstrated by means of the homometathesis of 1-octene and methyl oleate. In the metathesis of methyl oleate as natural raw material, the thermodynamic equilibrium can virtually be reached within 15 hours using catalyst 1 at an olefin:catalyst ratio of 500:1. In the metathesis of 1-octene, 7-tetradecene was not obtained as sole reaction product in all cases. An isomerization of 1-octene to 2-octene detected by NMR spectroscopy and subsequent olefin metathesis is responsible for this fact. Homometathesis and cross-metathesis of 1-octane and 2-octene gave not only 7-tetradecene but also 6-tridecene as main by-product and small amounts of 6-dodecene, 1-heptene and 2-nonene. The product distribution is strongly dependent on the catalyst used. In the case of 2, 7-tetradecene was obtained virtually selectively; in contrast, the more active complex 1 gave 7-tetradecene in a selectivity of only 63% at a high conversion. The by-product obtained was essentially 6-tridecene from the cross-metathesis of 1-octene with 2-octene.

Ring-Opening Metathesis Polymerization (ROMP) of 1,5-cyclooctadiene

ROMP of 1,5-cyclooctadiene. NMR comparison of a ruthenium-dicarbene complex with a ruthenium-carbene phosphine complex. (T=25° C.; 1.70 µmol of catalyst in 0.55 ml of $CD_2Cl_2$; [1,5-cyclooctadiene]/[catalyst]—250:1)

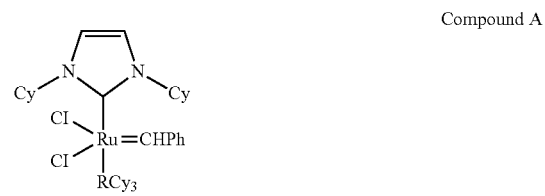

Compound A

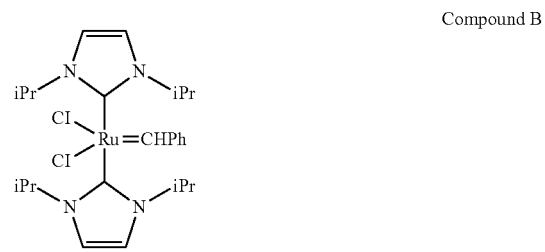

Compound B

The same applies to ROMP of cyclooctene:

ROMP of cyclooctadiene. NMR Kinetics of a ruthenium-dicarbene complex compared to a ruthenium-carbene phosphine complex. (T=25° C.; 2.50 µmol of catalyst in 0.50 ml of $CD_2Cl_2$; [cyclooctadiene]/[catalyst]—250:1.

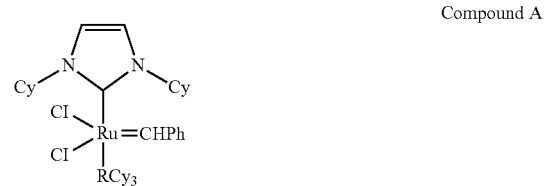

Compound A

-continued

Compound B

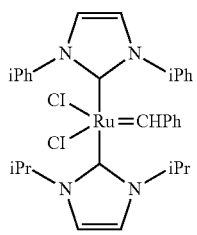

The invention claimed is:
1. A complex of ruthenium of the structural formula I,

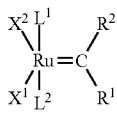

where $X^1$ and $X^2$ are identical or different and are each an anionic ligand, $R^1$ and $R^2$ are identical or different and are each hydrogen or a hydrocarbon group, where the hydrocarbon groups are identical or different and are selected independently from among straight-chain, branched, cyclic or noncyclic radicals from the group consisting of alkyl radicals having from 1 to 50 carbon atoms, alkenyl radicals having up to 50 carbon atoms, alkynyl radicals having up to 50 carbon atoms, aryl radicals having up to 30 carbon atoms and silyl radicals, or $R^1$ and $R^2$ form a ring, where one or more of the hydrogen atoms in the hydrocarbon or silyl groups or both the hydrocarbon and silyl group can be replaced independently by identical or different alkyl, aryl, alkenyl, alkynyl, metallocenyl, halogen, nitro, nitroso, hydroxy, alkoxy, aryloxy, amino, amido, carboxyl, carbonyl, thio or sulfonyl groups, the ligand $L^1$ is an N-heterocyclic carbene of the formulae II-V and the ligand $L^2$ is an N-heterocyclic carbene of the formulae III-V or an amine, imine, phosphine, phosphite, arsine, carbonyl compound, carboxyl compound, nitrile, alcohol, ether, thiol or thioether,

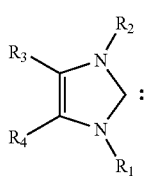

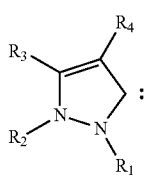

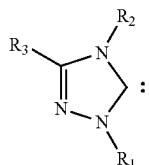

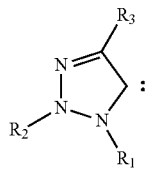

where $R_1$, $R_2$, $R_3$ and $R_4$ in the formulae II, III, IV and V are identical or different and are each hydrogen or a hydrocarbon group, where the hydrocarbon groups comprise identical or different, cyclic, noncyclic, straight-chain or/and branched radicals selected from the group consisting of alkyl radicals having from 1 to 50 carbon atoms, alkenyl radicals having up to 50 carbon atoms, alkynyl radicals having up to 50 carbon atoms and aryl radicals having up to 30 carbon atoms, in which at least one hydrogen may be replaced by functional groups, and where one or both of $R_3$ and $R_4$ may be identical or different halogen, nitro, nitroso, alkoxy, aryloxy, amido, carboxyl, carbonyl, thio or sulfonyl groups.

2. A complex as claimed in claim 1, wherein $R^3$ and $R^4$ in the formulae II, III, IV and V form a fused-on ring system.

3. A complex as claimed in claim 1, wherein $L^1$ and $L^2$ form a chelating ligand of the formula VI $$L^1\text{-}Y\text{-}L^2 \qquad \text{VI}$$

where the bridges Y comprise cyclic, noncyclic, straight-chain or branched radicals selected from the group consisting of alkylene radicals having from 1 to 50 carbon atoms, alkenylene radicals having up to 50 carbon atoms, alkynylene radicals having up to 50 carbon atoms, arylene radicals having up to 30 carbon atoms, metallocenylene, borylene and silylene radicals in which one or more hydrogens may be replaced independently by identical or different alkyl, aryl, alkenyl, alkynyl, metallocenyl, halo, nitro, nitroso, hydroxy, alkoxy, aryloxy, amino, amido, carboxyl, carbonyl, thio or sulfonyl groups.

4. A process for preparing acyclic olefins having two or more carbon atoms or cyclic olefins having four or more carbon atoms, in each case of the formula VII

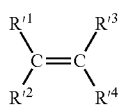

from acyclic olefins having two or more carbon atoms or from cyclic olefins having four or more carbon atoms, in each case corresponding to the formula VII by an olefin metathesis reaction in the presence of at least one catalyst comprising the complex as claimed in claim 1 and $R'^1$, $R'^2$, $R'^3$ and $R'^4$ in the formula VII are hydrogen or hydrocarbon groups, where the hydrocarbon groups are each selected independently from among straight-chain, branched, cyclic or noncyclic radicals of the group consisting of alkyl radicals having from 1 to 50 carbon atoms, alkenyl radicals having up to 50 carbon atoms, alkynyl radicals having up to 50 carbon atoms, aryl radicals having up to 30 carbon atoms, metallocenyl or silyl radicals, in which one or more hydrogens may be replaced by a functional group, where one or more $R^{l1}$, $R^{l2}$, $R^{l3}$ and $R^{l4}$ may independently be identical or different halogen, nitro, nitroso, hydroxy, alkoxy, aryloxy, amino, amido, carboxyl, carbonyl, thio, sulfonyl or metallocenyl groups.

5. The process as claimed in claim 4, wherein $R^{l1}$, $R^{l2}$, $R^{l3}$ and $R^{l4}$ in the olefins of the formula VII to be prepared form, in pairs, one or more identical or different rings.

6. A complex of ruthenium of the structural formula I,

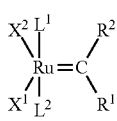

I where $X^1$ and $X^2$ are identical or different and are each an anionic ligand, $R^1$ and $R^2$ are identical or different and are each hydrogen or a hydrocarbon group, where the hydrocarbon groups are identical or different and are selected independently from among straight-chain, branched, cyclic or noncyclic radicals from the group consisting of alkyl radicals having from 1 to 50 carbon atoms, alkenyl radicals having up to 50 carbon atoms, alkynyl radicals having up to 50 carbon atoms, aryl radicals having up to 30 carbon atoms and silyl radicals, or $R^1$ and $R^2$ form a ring, where one or more of the hydrogen atoms in the hydrocarbon or silyl groups or both the hydrocarbon and silyl group can be replaced independently by identical or different alkyl, aryl, alkenyl, alkynyl, metallocenyl, halogen, nitro, nitroso, hydroxy, alkoxy, aryloxy, amino, amido, carboxyl, carbonyl, thio or sulfonyl groups or mixtures thereof, the ligand $L^1$ is an N-heterocyclic carbene and the ligand $L^2$ is N-heterocyclic carbene of the formulae III-V or an amine, imine, phosphine, stibine, arsine, carbonyl compound, carboxyl compound, nitrile, alcohol, ether, thiol or thioether and wherein formulae (III)-(V) are

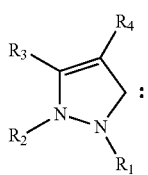

III

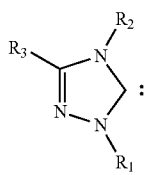

IV

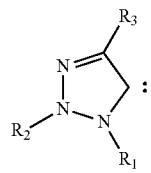

V where $R_1$, $R_2$, $R_3$ and $R_4$ in the formulae III, IV and V are identical or different and are each hydrogen or a hydrocarbon group, where the hydrocarbon groups comprise identical or different, cyclic, noncyclic, straight-chain or/and branched radicals selected from the group consisting of alkyl radicals having from 1 to 50 carbon atoms, alkenyl radicals having up to 50 carbon atoms, alkynyl radicals having up to 50 carbon atoms and aryl radicals having up to 30 carbon atoms, in which at least one hydrogen may be replaced by functional groups, and where one or both of $R_3$ and $R_4$ may be identical or different and are halogen, nitro, nitroso, alkoxy, aryloxy, amido, carboxyl, carbonyl, thio or sulfonyl groups.

7. A complex of ruthenium of the structural formula I,

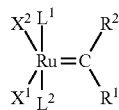

I where $X^1$ and $X^2$ are identical or different and are each an anionic ligand, $R^1$ and $R^2$ are identical or different and are each hydrogen or a hydrocarbon group, where the hydrocarbon groups are identical or different and are selected independently from among straight-chain, branched, cyclic or noncyclic radicals from the group consisting of alkyl radicals having from 1 to 50 carbon atoms, alkenyl radicals having up to 50 carbon atoms, alkynyl radicals having up to 50 carbon atoms, aryl radicals having up to 30 carbon atoms and silyl radicals, or $R^1$ and $R^2$ form a ring, where one or more of the hydrogen atoms in the hydrocarbon or silyl groups or both the hydrocarbon and silyl group can be replaced independently by identical or different alkyl, aryl, alkenyl, alkynyl, metallocenyl, halogen, nitro, nitroso, hydroxy, alkoxy, aryloxy, amino, amido, carboxyl, carbonyl, thio or sulfonyl groups or mixtures thereof, the ligand $L^1$ is an N-heterocyclic carbene and the ligand $L^2$ is N-heterocyclic carbene of the formulae III-V or an amine, imine, phosphine, phosphite, arsine, carbonyl compound, carboxyl compound, nitrile, alcohol, ether, thiol or thioether and wherein formulae (III)-(V) are

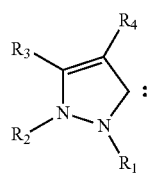

III

-continued

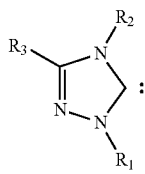
IV

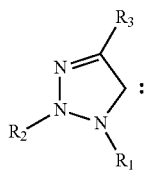
V where R₁, R₂, R₃ and R₄ in the formulae III, IV and V are identical or different and are each hydrogen or a hydrocarbon group, where the hydrocarbon groups comprise identical or different, cyclic, noncyclic, straight-chain or/and branched radicals selected from the group consisting of alkyl radicals having from 1 to 50 carbon atoms, alkenyl radicals having up to 50 carbon atoms, alkynyl radicals having up to 50 carbon atoms and aryl radicals having up to 30 carbon atoms, in which at least one hydrogen may be replaced by functional groups, and where one or both of $R_3$ and $R_4$ may be identical or different and are halogen, nitro, nitroso, alkoxy, aryloxy, amido, carboxyl, carbonyl, thio or sulfonyl groups.

8. A complex of ruthenium of the structural formula I,

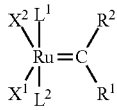
I where $X^1$ and $X^2$ are identical or different and are each an anionic ligand, $R^1$ and $R^2$ are identical or different and are each hydrogen or a hydrocarbon group, where the hydrocarbon groups are identical or different and are selected independently from among straight-chain, branched, cyclic or noncyclic radicals from the group consisting of alkyl radicals having from 1 to 50 carbon atoms, alkenyl radicals having up to 50 carbon atoms, alkynyl radicals having up to 50 carbon atoms, aryl radicals having up to 30 carbon atoms and silyl radicals, or $R^1$ and $R^2$ form a ring, where one or more of the hydrogen atoms in the hydrocarbon or silyl groups or both the hydrocarbon and silyl group can be replaced independently by identical or different alkyl, aryl, alkenyl, alkynyl, metallocenyl, halogen, nitro, nitroso, hydroxy, alkoxy, aryloxy, amino, amido, carboxyl, carbonyl, thio or sulfonyl groups or mixtures thereof, the ligand $L^1$ is an N-heterocyclic carbene and the ligand $L^2$ is N-heterocyclic carbene of the formulae III-V or an amine, imine, phosphine, phosphite, stibine, carbonyl compound, carboxyl compound, nitrile, alcohol, ether, thiol or thioether and wherein formulae (III)-(V) are

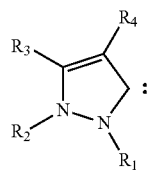
III

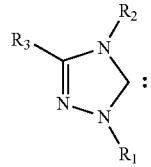
IV

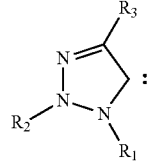
V

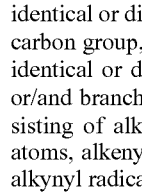

where R₁, R₂, R₃ and R₄ in the formulae III, IV and V are identical or different and are each hydrogen or a hydrocarbon group, where the hydrocarbon groups comprise identical or different, cyclic, noncyclic, straight-chain or/and branched radicals selected from the group consisting of alkyl radicals having from 1 to 50 carbon atoms, alkenyl radicals having up to 50 carbon atoms, alkynyl radicals having up to 50 carbon atoms and aryl radicals having up to 30 carbon atoms, in which at least one hydrogen may be replaced by functional groups, and where one or both of $R_3$ and $R_4$ may be identical or different and are halogen, nitro, nitroso, alkoxy, aryloxy, amido, carboxyl, carbonyl, thio or sulfonyl groups.

9. The complex as claimed in claim 8, wherein the ligand $L^2$ is phosphine.

10. The complex as claimed in claim 8, wherein the ligand $L^2$ is P(cyclohexyl)₃, or P(phenyl)₃.

11. The complex as claimed in claim 8, wherein $X^1$ and $X^2$ are halide, $R^1$ and $R^2$ are hydrogen or aryl or together form a ring and $L^2$ is a phosphine)

12. A process for preparing acyclic olefins having two or more carbon atoms or cyclic olefins having four or more carbon atoms, in each case of the formula VII

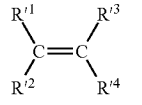
VII from acyclic olefins having two or more carbon atoms or from cyclic olefins having four or more carbon atoms, in each case corresponding to the formula VII by an olefin metathesis reaction in the presence of at least one catalyst comprising the complex as claimed in claim 8 and $R'^1$, $R'^2$, $R'^3$ and $R'^4$ in the formula VII are identical or different and are hydrogen or hydrocarbon groups, where the hydrocarbon groups are each selected independently from among straight-chain, branched, cyclic or noncyclic radicals of the group consisting of alkyl radicals having from 1 to 50 carbon atoms, alkenyl radicals having up to 50 carbon atoms, alkynyl radicals having up to 50 carbon atoms, aryl radicals having up to 30 carbon atoms, metallocenyl or silyl radicals, in which one or more hydrogens may be replaced by a functional group, where one or more of $R^{r1}$, $R^{r2}$, $R^{r3}$ and $R^{r4}$ may independently be identical or different halogen, nitro, nitroso, hydroxy, alkoxy, aryloxy, amino, amido, carboxyl, carbonyl, thio, sulfonyl or metallocenyl groups.)

13. The process as claimed in claim 12, wherein $R^{r1}$, $R^{r2}$, $R^{r3}$ and $R^{r4}$ in the olefins of the formula VII to be prepared form, in pairs, one or more identical or different rings.

14. In a process for olefin metathesis reaction wherein the improvement comprises using a catalyst which comprises the complex as claimed in claim 1.

15. In a process for olefin metathesis reaction wherein the improvement comprises using a catalyst which comprises the complex as claimed in claim 8.

16. An olefin metathesis process which comprises reacting an olefin with at least one double bond in the presence of a catalyst wherein said catalyst comprises the complex as claimed in claim 8.

17. A process for ring-opening metathesis polymer which comprises reacting an olefin with at least one double bond in the presence of a catalyst wherein said catalyst comprises the complex as claimed in claim 8.

18. A process for ring-closing metathesis which comprises reacting an olefin with at least one double bond in the presence of a catalyst wherein said catalyst comprises the complex as claimed in claim 8.

19. A process for acyclic diene metatheis polymerization which comprises reacting an olefin with at least one double bond in the presence of a catalyst wherein said catalyst comprises the complex as claimed in claim 8.

20. A process for depolymerization of an olefin polymer which comprises reacting an olefin with at least one double bond in the presence of a catalyst wherein said catalyst comprises the complex as claimed in claim 8.

21. An olefin metathesis process which comprises reacting an olefin with at least one double bond in the presence of a catalyst wherein said catalyst comprises the complex as claimed in claim 1.

22. A process for ring-opening metathesis polymer which comprises reacting an olefin with at least one double bond in the presence of a catalyst wherein said catalyst comprises the complex as claimed in claim 1.

23. A process for ring-closing metathesis which comprises reacting an olefin with at least one double bond in the presence of a catalyst wherein said catalyst comprises the complex as claimed in claim 1.

24. A process for acyclic diene metatheis polymerization which comprises reacting an olefin with at least one double bond in the presence of a catalyst wherein said catalyst comprises the complex as claimed in claim 1.

25. A process for depolymerization of an olefin polymer which comprises reacting an olefin with at least one double bond in the presence of a catalyst wherein said catalyst comprises the complex as claimed in claim 1.

26. In a process for olefin metathesis reaction wherein the improvement comprises using a catalyst which comprises the complex as claimed in claim 11.

27. An olefin metathesis process which comprises reacting an olefin with at least one double bond in the presence of a catalyst wherein said catalyst comprises the complex as claimed in claim 11.

28. A process for ring-opening metathesis polymer which comprises reacting an olefin with at least one double bond in the presence of a catalyst wherein said catalyst comprises the complex as claimed in claim 11.

29. A process for ring-closing metathesis which comprises reacting an olefin with at least one double bond in the presence of a catalyst wherein said catalyst comprises the complex as claimed in claim 11.

30. A process for acyclic diene metatheis polymerization which comprises reacting an olefin with at least one double bond in the presence of a catalyst wherein said catalyst comprises the complex as claimed in claim 11.

31. A process for depolymerization of an olefin polymer which comprises reacting an olefin with at least one double bond in the presence of a catalyst wherein said catalyst comprises the complex as claimed in claim 11.

32. The complex as claimed in claim 1, wherein $R_3$ and $R_4$ are identical or different and are hydrogen, a hydrocarbon group, halogen or a carboxyl group.

33. The complex as claimed in claim 8, wherein $R_3$ and $R_4$ are identical or different and are hydrogen, a hydrocarbon group, halogen or a carboxyl group.

34. The complex as claimed in claim 8, wherein the ligand $L^1$ is a five membered N-heterocyclic carbene.

35. The complex as claimed in claim 11, wherein the ligand $L^1$ is a five membered N-heterocyclic carbene.

* * * * *